United States Patent
Sadowski et al.

[11] Patent Number: 5,643,211
[45] Date of Patent: Jul. 1, 1997

[54] NOZZLE ASSEMBLY HAVING A FRANGIBLE PLUNGER

[75] Inventors: Peter Sadowski, Woodbury, Minn.; Paul Mulhauser, New York, N.Y.; David Schiff, Highland Park, N.J.

[73] Assignee: Medi-Ject Corporation, Minneapolis, Minn.

[21] Appl. No.: 608,799

[22] Filed: Feb. 29, 1996

[51] Int. Cl.$^6$ ..................................... A61M 5/00
[52] U.S. Cl. .................... 604/110; 604/218; 604/228
[58] Field of Search .................... 604/110, 187, 604/218, 228

[56] References Cited

U.S. PATENT DOCUMENTS

| | | |
|---|---|---|
| D. 304,616 | 11/1989 | Dunlap et al. . |
| D. 349,958 | 8/1994 | Hollis et al. . |
| 396,107 | 1/1889 | Nickerson . |
| 489,757 | 1/1893 | Reilly . |
| 1,567,517 | 12/1925 | Kisbey . |
| 1,973,706 | 9/1934 | Hawley . |
| 2,322,244 | 6/1943 | Lockhart . |
| 2,322,245 | 6/1943 | Lockhart . |
| 2,380,534 | 7/1945 | Lockhart . |
| 2,390,246 | 12/1945 | Folkman . |
| 2,398,544 | 4/1946 | Lockhart . |
| 2,413,303 | 12/1946 | Folkman . |
| 2,459,875 | 1/1949 | Folkman . |
| 2,547,099 | 4/1951 | Smoot . |
| 2,605,763 | 8/1952 | Smoot . |
| 2,635,602 | 4/1953 | Hein . |
| 2,653,602 | 9/1953 | Smoot . |
| 2,670,121 | 2/1954 | Scherer et al. . |
| 2,671,347 | 3/1954 | Scherer . |
| 2,681,653 | 6/1954 | Kuhne . |
| 2,688,968 | 9/1954 | Scherer . |
| 2,699,166 | 1/1955 | Dickinson, Jr. et al. . |
| 2,704,542 | 3/1955 | Scherer . |
| 2,704,543 | 3/1955 | Scherer . |
| 2,705,953 | 4/1955 | Potez . |
| 2,714,887 | 8/1955 | Venditty . |
| 2,717,597 | 9/1955 | Hein, Jr. . |
| 2,737,946 | 3/1956 | Hein, Jr. . |
| 2,754,818 | 7/1956 | Scherer . |
| 2,762,369 | 9/1956 | Venditty . |
| 2,762,370 | 9/1956 | Venditty . |
| 2,764,977 | 10/1956 | Ferguson . |
| 2,789,839 | 4/1957 | Siebert . |
| 2,798,485 | 7/1957 | Hein, Jr. . |
| 2,798,486 | 7/1957 | Hein, Jr. . |
| 2,800,903 | 7/1957 | Smoot . |
| 2,816,543 | 12/1957 | Venditty et al. . |
| 2,816,544 | 12/1957 | Scherer et al. . |
| 2,820,655 | 1/1958 | Hileman . |
| 2,821,193 | 1/1958 | Ziherl et al. . |
| 2,821,981 | 2/1958 | Ziherl et al. . |

(List continued on next page.)

FOREIGN PATENT DOCUMENTS

| | | |
|---|---|---|
| 2028870 | 5/1991 | Canada . |
| 2071115 | 12/1992 | Canada . |
| 0157906 | 10/1985 | European Pat. Off. . |
| 0460961 | 6/1991 | European Pat. Off. . |
| 959397 | 6/1964 | United Kingdom . |

OTHER PUBLICATIONS

Catalog: Hoechst Celanese—Advanced Materials Group, "Vectra® Liquid Crystal Polymer".

*Primary Examiner*—John D. Yasko
*Attorney, Agent, or Firm*—Pennie & Edmonds

[57] ABSTRACT

A nozzle assembly adapted for an injector, includes a frangible plunger. The plunger has a first driving member and a second driving member connected to the first driving member and spaced apart therefrom by a predetermined gap using a frangible bridge. When a predetermined force is applied to the second driving member, it breaks the frangible bridge and moves the second driving member across the gap. This causes the second driving member to ram into the first driving member driving fluid out of the nozzle. Thereafter, as the second driving member is separated from the first driving member, the first driving member remains stuck in the chamber preventing reuse of the nozzle assembly.

20 Claims, 3 Drawing Sheets

U.S. PATENT DOCUMENTS

| | | |
|---|---|---|
| 2,825,332 | 3/1958 | Johnson . |
| 2,902,994 | 9/1959 | Scherer . |
| 2,921,582 | 1/1960 | Sadd . |
| 2,928,390 | 3/1960 | Venditty et al. . |
| 3,057,349 | 10/1962 | Ismach . |
| 3,066,670 | 12/1962 | Stauffer . |
| 3,115,133 | 12/1963 | Morando . |
| 3,123,070 | 3/1964 | Kath . |
| 3,129,708 | 4/1964 | Krantz . |
| 3,130,723 | 4/1964 | Venditty et al. . |
| 3,131,692 | 5/1964 | Love . |
| 3,138,157 | 6/1964 | Ziherl et al. . |
| 3,140,713 | 7/1964 | Ismach . |
| 3,147,967 | 9/1964 | Bougeard . |
| 3,167,071 | 1/1965 | Venditty . |
| 3,189,029 | 6/1965 | Stephens . |
| 3,202,151 | 8/1965 | Kath . |
| 3,245,703 | 4/1966 | Manly . |
| 3,292,622 | 12/1966 | Banker . |
| 3,308,818 | 3/1967 | Rutkowski . |
| 3,330,276 | 7/1967 | Gordon . |
| 3,330,277 | 7/1967 | Gabriels . |
| 3,335,722 | 8/1967 | Lowry et al. . |
| 3,353,537 | 11/1967 | Knox et al. . |
| 3,406,684 | 10/1968 | Tsujino . |
| 3,424,154 | 1/1969 | Kinsley . |
| 3,461,867 | 8/1969 | Zimmet et al. . |
| 3,476,110 | 11/1969 | Yahner . |
| 3,490,451 | 1/1970 | Yahner . |
| 3,507,276 | 4/1970 | Burgess . |
| 3,518,990 | 7/1970 | Banker . |
| 3,521,633 | 7/1970 | Yahner . |
| 3,526,225 | 9/1970 | Isobe . |
| 3,527,212 | 9/1970 | Clark . |
| 3,557,784 | 1/1971 | Shields . |
| 3,561,443 | 2/1971 | Banker . |
| 3,625,208 | 12/1971 | Frost et al. . |
| 3,659,587 | 5/1972 | Baldwin . |
| 3,688,765 | 9/1972 | Gasaway . |
| 3,714,943 | 2/1973 | Yanof et al. . |
| 3,768,472 | 10/1973 | Hodosh et al. . |
| 3,779,371 | 12/1973 | Rovinski . |
| 3,782,380 | 1/1974 | van der Gaast . |
| 3,783,895 | 1/1974 | Weichselbaum . |
| 3,788,315 | 1/1974 | Laurens . |
| 3,805,783 | 4/1974 | Ismach . |
| 3,827,601 | 8/1974 | Magrath et al. . |
| 3,838,689 | 10/1974 | Cohen . |
| 3,908,651 | 9/1975 | Fudge . |
| 3,938,520 | 2/1976 | Scislowicz et al. . |
| 3,945,379 | 3/1976 | Pritz et al. . |
| 3,945,383 | 3/1976 | Bennett et al. . |
| 4,026,212 | 5/1977 | Dardick ................. 102/39 |
| 4,059,107 | 11/1977 | Iriguchi et al. . |
| 4,089,334 | 5/1978 | Schwebel et al. . |
| 4,141,675 | 2/1979 | O'Neill .................. 417/214 |
| 4,328,802 | 5/1982 | Curley et al. . |
| 4,387,879 | 6/1983 | Tauschinski . |
| 4,421,508 | 12/1983 | Cohen . |
| 4,447,225 | 5/1984 | Taff et al. . |
| 4,500,075 | 2/1985 | Tsuchiya et al. . |
| 4,505,709 | 3/1985 | Froning et al. . |
| 4,507,113 | 3/1985 | Dunlap . |
| 4,518,385 | 5/1985 | Lindmayer et al. . |
| 4,561,856 | 12/1985 | Cochran . |
| 4,588,403 | 5/1986 | Weiss et al. . |
| 4,596,556 | 6/1986 | Morrow et al. . |
| 4,619,651 | 10/1986 | Kopfer et al. . |
| 4,623,332 | 11/1986 | Lindmayer et al. . |
| 4,626,242 | 12/1986 | Fejes et al. . |
| 4,662,878 | 5/1987 | Lindmayer . |
| 4,675,020 | 6/1987 | McPhee . |
| 4,680,027 | 7/1987 | Parsons et al. . |
| 4,709,686 | 12/1987 | Taylor et al. . |
| 4,722,728 | 2/1988 | Dixon . |
| 4,744,786 | 5/1988 | Hooven . |
| 4,768,568 | 9/1988 | Fournier et al. . |
| 4,771,758 | 9/1988 | Taylor et al. . |
| 4,775,173 | 10/1988 | Sauer . |
| 4,790,824 | 12/1988 | Morrow et al. . |
| 4,834,149 | 5/1989 | Fournier et al. . |
| 4,850,967 | 7/1989 | Cosmai . |
| 4,863,427 | 9/1989 | Cocchi ................. 604/110 |
| 4,874,367 | 10/1989 | Edwards . |
| 4,883,483 | 11/1989 | Lindmayer . |
| 4,909,488 | 3/1990 | Seibert et al. . |
| 4,923,072 | 5/1990 | Rilliet . |
| 4,940,460 | 7/1990 | Casey et al. . |
| 4,941,880 | 7/1990 | Burns . |
| 4,948,104 | 8/1990 | Wirges . |
| 4,989,905 | 2/1991 | Rajecki . |
| 5,031,266 | 7/1991 | Tillman et al. . |
| 5,041,715 | 8/1991 | Muller . |
| 5,061,263 | 10/1991 | Yamazaki et al. . |
| 5,062,830 | 11/1991 | Dunlap . |
| 5,064,413 | 11/1991 | McKinnon et al. . |
| 5,066,280 | 11/1991 | Braithwaite ............ 604/218 X |
| 5,073,165 | 12/1991 | Edwards . |
| 5,085,332 | 2/1992 | Gettig et al. . |
| 5,116,313 | 5/1992 | McGregor . |
| 5,135,507 | 8/1992 | Haber et al. . |
| 5,161,786 | 11/1992 | Cohen . |
| 5,165,560 | 11/1992 | Ennis, III et al. . |
| 5,176,406 | 1/1993 | Straghan . |
| 5,188,599 | 2/1993 | Botich et al. ............ 604/110 |
| 5,190,523 | 3/1993 | Lindmayer . |
| 5,193,517 | 3/1993 | Taylor et al. . |
| 5,209,362 | 5/1993 | Lutzker . |
| 5,224,932 | 7/1993 | Lappas .................. 604/80 |
| 5,226,882 | 7/1993 | Bates . |
| 5,292,308 | 3/1994 | Ryan . |
| 5,304,128 | 4/1994 | Haber et al. . |
| 5,312,335 | 5/1994 | McKinnon et al. . |
| 5,312,577 | 5/1994 | Peterson et al. . |
| 5,316,198 | 5/1994 | Fuchs et al. . |
| 5,334,144 | 8/1994 | Alchas et al. . |
| 5,356,380 | 10/1994 | Hoekwater et al. . |
| 5,360,146 | 11/1994 | Ikushima . |
| 5,383,851 | 1/1995 | McKinnon, Jr. et al. . |
| 5,399,163 | 3/1995 | Peterson et al. . |
| 5,407,431 | 4/1995 | Botich et al. . |
| 5,413,471 | 5/1995 | Yamauchi ............ 425/129.1 |
| 5,423,756 | 6/1995 | van der Merwe . |
| 5,499,972 | 3/1996 | Parsons ................. 604/68 |

NOZZLE ASSEMBLY HAVING A FRANGIBLE PLUNGER

TECHNICAL FIELD

The present invention relates to an injector nozzle assembly having a plunger made out of two halves separated by a gap therebetween and connected by a frangible bridge.

BACKGROUND

Medical communities have become concerned over the possibility of accidental communication of disease, such as Acquired Immune Deficiency Syndrome (AIDS), hepatitis, and other diseases communicable through bodily fluids, through accidental needle sticking and improperly sterilized multiple-use needle injector. One way to curb some of these mishaps is to discard the entire needle injector after a single use.

A number of single use needle injectors have been contemplated in this regard, as described in U. S. Pat. Nos. 5,226,882 to Bates; 5,423,756 to van der Merwe; 5,135,507 to Haber et al; and 5,407,431 to Botich et al. As with all needle injectors, they provide a barrel for holding medication and a plunger/piston assembly slidingly received within the barrel for ejecting medication out of the barrel The Bates and van der Merwe patents disclose a piston (the forefront part that pushes medication) that separates from a plunger (the rod-like portion that pushes the piston) after medication is ejected. The Haber and Botich patents achieves a similar result by locking the piston to the barrel after the injection stroke is completed to prevent reuse.

Needleless injectors have no needle. They thus completely remove any apprehension or the possibility of being pierced. At least in this regard, the needleless injectors are superior in eliminating accidental disease transmission. Different needleless injector types have been contemplated, as described, for instance, in U.S. Pat. Nos. 5,062,830 issued to Dunlap; 4,790,824 to Morrow et al.; 4,623,332 to Lindmayer et al.; 4,421,508 to Cohen; 4,089,334 to Schwebel et al.; 3,688,765 to Gasaway; 3,115,133 to Morando; 2,816, 543 to Venditty et al.; and 2,754,818 to Scherer. These injectors have been contemplated to administer medication as a fine, high velocity jet, delivered under sufficient pressure to enable the jet to pass through the skin tissue without requiring a hypodermic needle. These injectors typically have a nozzle assembly which has a barrel-like nozzle body for holding medication therein. The nozzle member has an orifice through which a jet stream of medication is forced out from the chamber when a plunger/piston is actuated by an energy source, such as a coil spring, gas spring, and gas cartridge.

Even though needleless injectors eliminate known problems associated with the needle injector type, nevertheless, as an added safety precaution, it would be desirable to discard the nozzle assembly after each use to prevent its reuse. For example, after a single use the high pressure applied by the energy source may cause the seal between the plunger/piston and the nozzle assembly to partially fail or leak. Thereafter, a subsequent use of the same nozzle may have inadequate pressure transmitted to the medication to ensure proper delivery. Additionally, this high pressure may enlarge the orifice in the nozzle assembly so that subsequent uses of the same assembly would not produce a jet having sufficient velocity to penetrate to a desired depth.

SUMMARY

The present invention relates to a single use nozzle assembly adapted for use with an injector device comprising a chamber for holding a fluid and having first and second ends with an orifice at the first end for passage of the fluid and being open at the second end, and a plunger slidingly received in the chamber for expelling fluid out of or drawing fluid into the chamber by moving the plunger relative to the chamber. The plunger comprises first and second driving members and a frangible connection therebetween, with the second driving member being spaced apart from the first driving member by a gap. Thus, when a force sufficient to break the frangible connection is applied to the second driving member in a direction toward the first driving member, the frangible connection is broken and the second driving member moves across said gap toward the first driving member for urging the first driving member towards the chamber orifice to expel fluid therefrom. Thereafter, when the second driving member is moved away from the first driving member, the first driving member remains in the chamber to prevent reuse of the nozzle assembly.

The frangible connection preferably has a smaller cross-sectional area than either of the first and second driving members and is disposed perpendicular to the longitudinal axis of the first and second driving members. Advantageously, the first and second driving members are spaced apart and joined together by a frangible connection. First and second driving members are positioned, such that when the frangible connection is broken the space between the driving members is collapsed. Particularly, the first and second driving members can be cylindrical and have D-shaped end portions which face each other and are joined by the frangible connection, and the frangible connection is a rectangular bridge connecting straight sides of the D-shaped portions of the first and second driving members.

Preferably, the first driving member has a seal in contact with an inner wall of the chamber to prevent fluid from exiting the chamber around the first driving member and through the open end. Also, the chamber includes a connector adapted for connecting the nozzle to the injector, and it may include external ridges or threads for connection to an injection device.

If desired, the second driving member may include an end post which can be grasped to move the second driving member in a direction away from the chamber orifice to either draw fluid into the chamber or to remove the second driving member from the chamber. This movement can also dispel air from the chamber before introduction of the liquid therein. To assist in the movement of fluid, the chamber may include a tapered portion adjacent the orifice and the first driving member may include a tapered cone which conforms to the tapered portion of the chamber.

BRIEF DESCRIPTION OF THE DRAWINGS

A better understanding of the invention may be obtained from a review of the appended drawing figures, which illustrate preferred embodiments and wherein.

DETAILED DESCRIPTION OF THE DRAWINGS

Figure 1:
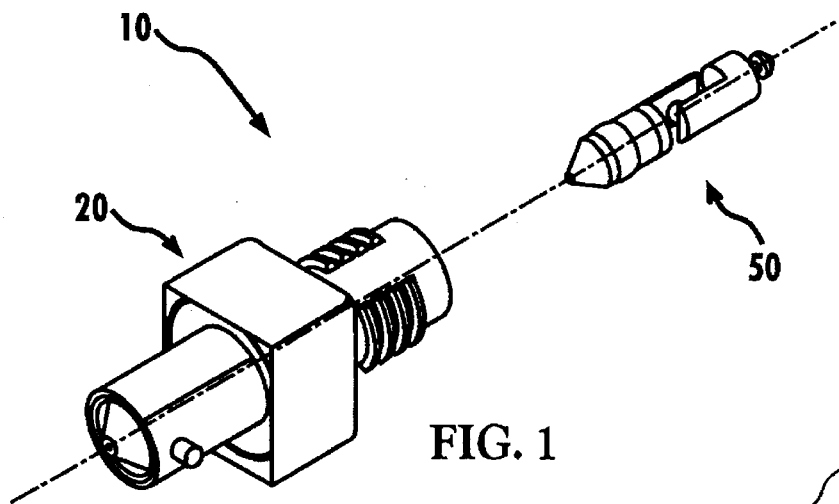
FIG. 1 is an exploded perspective view of a nozzle assembly according to the present invention.

The nozzle assembly 10 according to the present invention is adapted for use with any conventional injector, including the needleless type disclosed in the aforementioned patents, the disclosure of which is incorporated herein by reference. When a needle type injector is to be used, the orifice is in fluid communication with the bore of an appropriately sized needle.

The assembly 10 has a nozzle member 20 having an orifice 22 of a suitable diameter that would produce a uniform jet stream under a given desired pressure range and depth of injection. Preferably, this diameter may be about 0.07–0.4 mm, and most preferably about 0.165 mm (0.0065 inches). If a highly precise jet stream is desired, the orifice can be formed of a synthetic gem material, such as a synthetic ruby or sapphire, as disclosed in U.S. Pat. No. 4,722,728 to Dixon. Hereinafter, the term "orifice" shall mean any type of opening, including a straight, convergent, divergent, convergent-divergent, etc.

The orifice may also be used to withdraw a fluid or liquid medication into the chamber. In this regard, a medication filling device such as an adapter for filling the internal chamber of a nozzle assembly from a liquid medication supply vial directly through the ejection orifice can be used to fill the chamber with medication, as described in U.S. Pat. Nos. 4,507,113 to Dunlap; and 4,883,483 and 4,662,878 to Lindmayer, the disclosure of which is incorporated herein by reference. Other coupling devices can also be used if desired.

The nozzle member 20, as shown in FIGS. 5A–5E, includes a cylindrical ampule chamber 26 terminating in a right circular cone 28. The chamber includes external ridges 40 for attachment to an injection device. The plunger 50 has a pressure wall contoured to the cone 28 and is received through an open end of the chamber. It is positioned to slide longitudinally within the ampule chamber 26 to expel fluid medication out of the chamber and may also draw fluid medication into the chamber.

Figure 4:
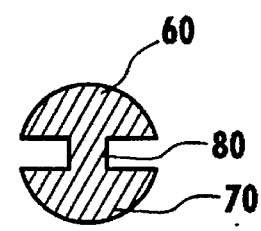
FIG. 4 is a cross sectional view taken along line 4—4 of FIG. 2.
Figure 2:
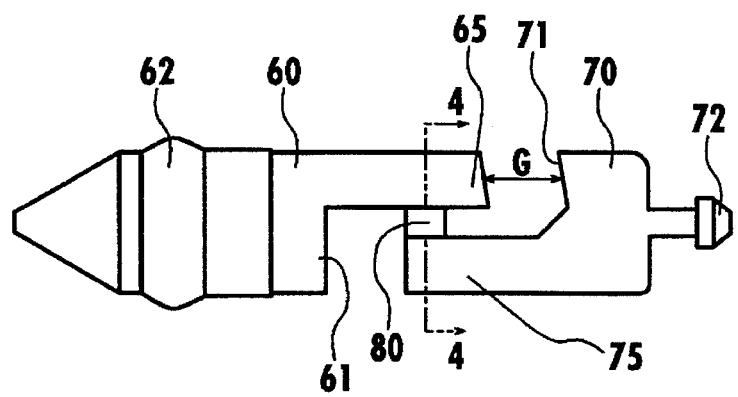
FIG. 2 is an elevational view of a frangible plunger according to the present invention, showing the plunger before injection.
Figure 3:
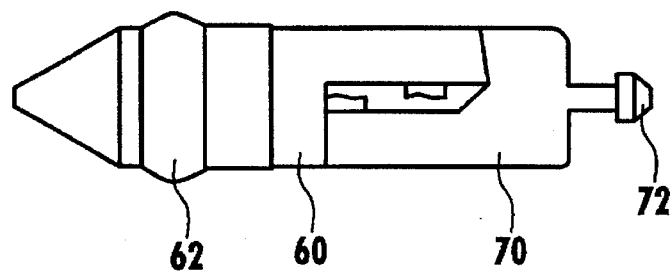
FIG. 3 is a view similar to FIG. 2, but with the plunger during or after injection.

As better shown in FIGS. 2 and 3, this plunger 50 is frangible and has a first driving member 60 and a second driving member 70. As shown, these members have a generally cylindrical shape with D-shaped end portions 65, 75. These driving members are connected together in a spaced apart relationship across a predetermined gap G by a frangible connection or bridge 80. Each end portion 65, 75 is spaced relative to an opposed base portion 71, 61, respectively. As shown in FIG. 4, the preferred frangible bridge 80 is a relatively thin rectangular member connecting the D-shaped end portion of the first driving member 60 to that of the second driving member 70. Advantageously, the frangible bridge 80 has a square cross-section. The frangible bridge 80 may be disposed in a perpendicular position to both straight sides of the D-shaped end portions 65, 75 of the first and second driving members as well as to the longitudinal axis of the first and second driving members, which are parallel to the longitudinal axis (direction of the sliding movement) of the plunger. Preferably, the plunger, including the frangible bridge is made out of a plastic, such as polycarbonate or polypropylene and is configured and dimensioned such that frangible bridge 80 can withstand a force "p" for moving or withdrawing the plunger to draw liquid medication into ampule 26 without breaking.

Alternatively, the frangible plunger 50 can be used with a prefilled ampule, thereby eliminating the need for moving the plunger longitudinally to draw liquid medication into ampule 26 or to expel excess liquid or bubbles therefrom.

The leading end of the first driving member 60 includes a seal 62, such as 0-ring or the like, preferably formed around its outer periphery to provide a seal with the inner wall of the chamber. The plunger itself can be a seal. Other seals or seal members can be included in the trailing end of the second driving member if desired to provide a better seal to prevent leakage of fluid for the chamber by minimizing the entry of air into the chamber from around the first and second driving member and by preventing air from entering the orifice due to liquid exiting the chamber around the driving members.

Figure 5A:
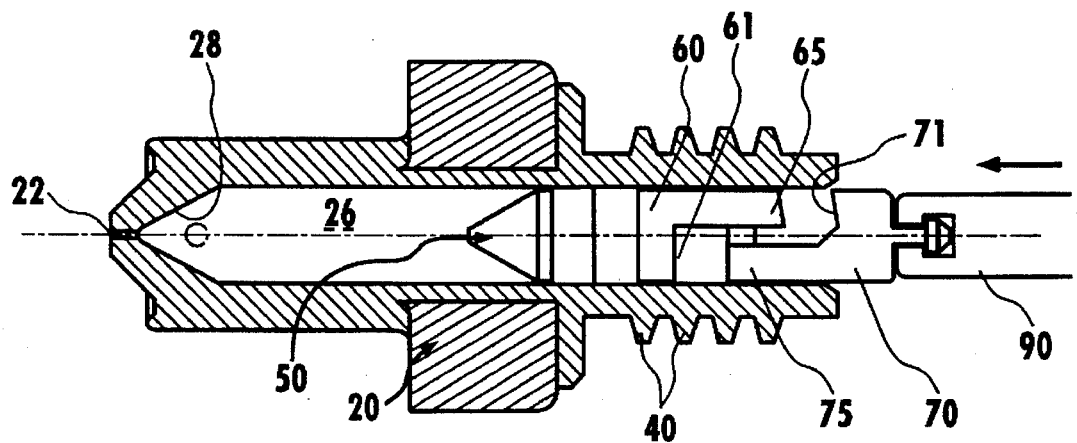
FIG. 5A is a cross-sectional view of the present nozzle assembly with the plunger pulled away from the nozzle member.

Referring to FIGS. 5A–5E, the nozzle assembly is attached to an injector body by connecting the end post 72 of the second driving member to the ram 90 of the injector, as shown in FIG. 5A, and connecting the bayonet mount 40 to the front of the injector body (not shown). The connection between the plunger and the ram 90 can be any conventional connection that holds these elements together but enables separation, such as a ball and slot configuration as depicted.

Figure 5B:
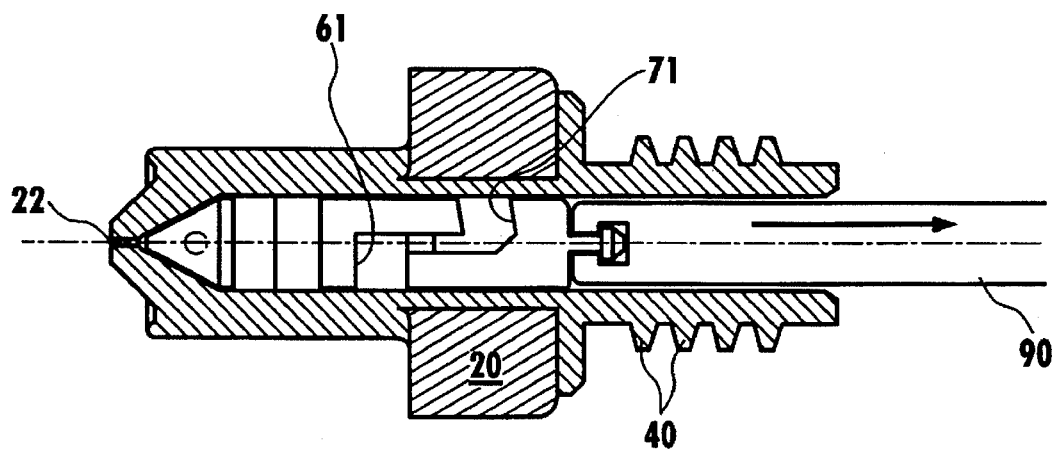
FIG. 5B is a cross-sectional view of the present nozzle assembly before withdrawing medication into the ampule chamber.
Figure 5C:
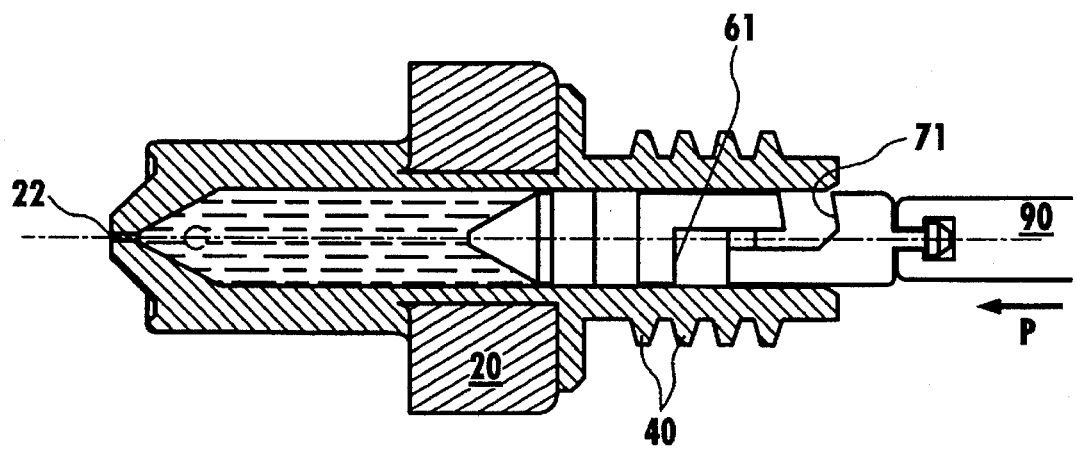
FIG. 5C is a view of the injector of the present injector after medication has been introduced into the barrel of the injector.

The plunger is pushed into the chamber, in the direction shown by the arrow in FIG. 5A, to purge air. FIG. 5B shows the plunger fully pushed, before the liquid medication is drawn into the chamber. As the plunger is pulled to the direction shown by the arrow in FIG. 5B, a partial vacuum is established inside the chamber and liquid medication is drawn into the chamber through the orifice.

Figure 5D:
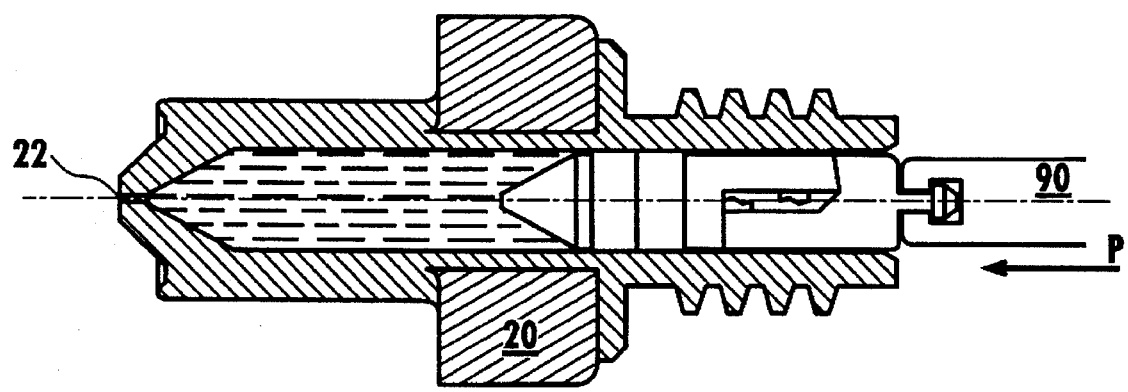
FIG. 5D is a view of the injector of the present invention after the frangible member of the piston is broken.
Figure 5E:
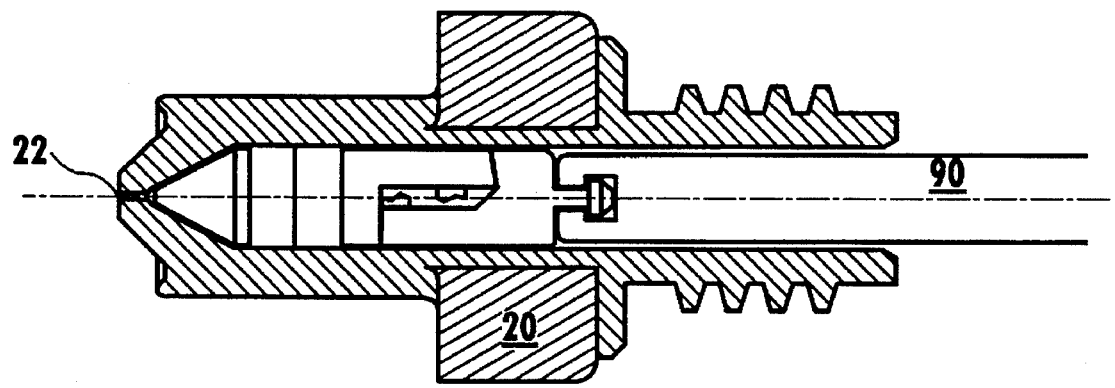
FIG. 5E is a view of the injector of the present invention after the piston has pushed the liquid out of the barrel.

It will be noted that the frangible connection is dimensioned and configured such that pushing or pulling action requiring force "p" normally affiliated with withdrawal and slow ejection of air or medication before injection does not break the bridge. Upon an application of a relatively large injection force "P" on the ram, which may be significantly larger than the force "p", the ram transmits this force P to the second driving member and breaks the frangible bridge. This allows the second driving member to close the gap and transmit force to the first driving member to eject medication out of the chamber, as shown in FIG. 5D. Finally, FIG. 5E shows the position where the injection is completed and all the medication has been ejected. At this point, the nozzle assembly can be rotated until the ridges 40 are free of the injection device and it can be removed. Since the first driving member is broken away from the second driving member, which remains connected to the ram, the first driving member remains inside the chamber. The second driving member is then removed from the ram and discarded along with the nozzle assembly. This prevents unwanted reuse of the nozzle assembly.

In a normal operation of the injector, ram 90 of the injection device operatively connected to an energy source imparts sudden force or impact P to the second driving member, enough to drive the second member into the first member. This action is sufficient to drive the liquid contained in ampule 26 outward through orifice 22 as a peak jet stream pressure for example in excess of 5,000 psi out of the orifice 22. This sudden force is capable of breaking the frangible bridge 80 before the injection begins. Specifically, the force P applied to the second driving member is transmitted to the first driving member through the bridge. Initially, the frictional force in the seal 62 generates enough friction to momentarily prevent the plunger from moving. Once this frictional force is overcome, the plunger starts to move and imparts pressure to the medication in the chamber. This creates resistance or back pressure on the first driving member. When the difference between the resistance force imparted to first driving member by the fluid and the force imparted by the second driving member toward the first driving member reaches a predetermined level, the bridge 80 breaks and the second driving member rams into the first driving member. Moreover, as shown in FIG. 3, end portion 75 of second driving member 70 rams into base portion 61 of first driving member 60 and base portion 71 of second driving member 70 rams into end portion 65 of first driving member 60.

Alternatively, frangible bridge 80 may be broken by an intermediate force larger than the force p, before the relatively large injection force P is applied on ram 90. Such an intermediate force can be generated for example by a pressure exerted on the liquid contained in ampule chamber 26 through orifice 22 or by other triggering mechanism.

The gap G plays an important role in creating a preferred pressure spike necessary to pierce through the patient's skin. Changing the gap G will change the initial force imparted on the first driving member. The peak pressure thus can be varied with the gap G. It can also vary depending upon the viscosity of the medication, the desired injection penetration depth and other parameters which may affect the initial injection pressure output. One of ordinary skill in the art can determine by routine experimentation the optimum gap for any frangible plunger that is to be used with a particular medication. Advantageously, frangible plunger 50 or nozzle assembly or both can be manufactured with different colors, wherein each color denotes a predetermined width of gap G. This color coding scheme will assist the user in choosing a proper nozzle assembly for a specific application.

Once the first and second driving members are separated, the first driving member remains stuck in the chamber. The chamber and the plunger thus becomes unusable. The amount of force to break the gap can be adjusted by changing the dimension of the bridge. Additionally, scoring lines or lines of breakage can be provided to controllably break the bridge. These can also be determined by routine experimentation to optimum performance criteria.

The nozzle assembly 10 can be connected to an injection device using any known structure for attaching and detaching two components together. The present invention preferably contemplates a bayonet-mount, which has diametrically opposed ridges 40. These ridges 40 are first aligned in an opening having a similar cross-sectional configuration provided in an injector so that the ridges can be inserted. Thereafter, the nozzle member 20 is rotated relative to the injector body by a predetermined degree to prevent the nozzle body from detaching in the axial direction. The bayonet-mount enables a quick attachment and detachment of the nozzle assembly. Alternatively, threads can be used to secure the nozzle assembly to the injection device. Other connection means can be used, if desired for a particular application.

It will be understood that the frangible plunger according to the present invention can also be used with syringes having hypodermic needles where the frangible bridge breaks either before the injection begins or after the completion of the injection.

It should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A nozzle assembly adapted for use with an injector device comprising:

a chamber for holding a fluid and having first and second ends with an orifice at the first end for passage of the fluid and being open at the second end; and a plunger slidingly received in said chamber for expelling fluid out of or drawing fluid into the chamber by moving the plunger relative to the chamber, the plunger comprising first and second driving members which include respective end and base portions retained in spaced relation by a frangible connection therebetween, with the second driving member being spaced apart from the first driving member by a gap, such that when a force sufficient to break the frangible connection is applied to the second driving member in a direction toward the first driving member, the frangible connection is broken and the second driving member moves across said gap toward the first driving member, the frangible connection is broken and the second driving member moves across said gap toward the first driving member for urging the first driving member towards the chamber orifice to expel fluid therefrom, and when the second driving member is thereafter moved away from the first driving member, the first driving member remains in the chamber to prevent reuse of the nozzle assembly.

2. The nozzle assembly according to claim 1, wherein the frangible connection has a smaller cross-sectional area than either of the first and second driving members.

3. The nozzle assembly according to claim 1, wherein the first driving member has a seal in contact with an inner wall of the chamber to prevent fluid from exiting the chamber around the first driving member and through the open end.

4. The nozzle assembly according to claim 1, wherein the chamber includes a connector adapted for connecting the nozzle to the injector.

5. The nozzle assembly according to claim 1, wherein the frangible connection is disposed perpendicular to the longitudinal axis of the end portions of the first and second driving members.

6. The nozzle assembly of claim 1 wherein the second driving member includes an end post which can be grasped to move the second driving member in a direction away from the chamber orifice to either draw fluid into the chamber or to remove the second driving member from the chamber.

7. The nozzle assembly of claim 1 wherein the chamber includes a tapered portion adjacent the orifice and the first driving member includes a tapered cone which conforms to the tapered portion of the chamber.

8. The nozzle assembly of claim 1 wherein the first and second driving members are cylindrical and have D-shaped end portions which face each other and are joined by the frangible connection.

9. The nozzle assembly of claim 8 wherein the frangible connection is a rectangular bridge connecting straight sides of the D-shaped portions of the first and second driving members.

10. A nozzle assembly adapted for use with an injector device comprising:

a chamber for holding a fluid and having first and second ends with an orifice at the first end for passage of the fluid and being open at the second end; and a plunger slidingly received in said chamber for expelling fluid out of or drawing fluid into the chamber by moving the plunger relative to the chamber, the plunger comprising first and second driving members and a frangible connection therebetween, with the second driving member being spaced apart from the first driving member by a gap, such that when a force sufficient to break the frangible connection is applied to the second driving member in a direction toward the first driving member, the frangible connection is broken and the second driving member moves across said gap toward the first driving member, the frangible connection is broken and the second driving member moves across said gap toward the first driving member for urging the first driving member towards the chamber orifice to expel fluid therefrom, and when the second driving member is thereafter moved away from the first driving member, the first driving member remains in the chamber to prevent reuse of the nozzle assembly, wherein the chamber includes external ridges or threads for connection to an injection device.

11. A nozzle assembly adapted for use with an injector device comprising:

a chamber for holding a fluid and having first and second ends with an orifice at the first end for passage of the fluid and being open at the second end; and a plunger slidingly received in said chamber for expelling fluid out of or drawing fluid into the chamber by moving the plunger relative to the chamber, the plunger comprising first and second driving members which include respective end and base portions retained in spaced relation by a frangible connection therebetween, with the second driving member being spaced apart from the first driving member by a gap, such that when a force sufficient to break the frangible connection is applied to the plunger, the frangible connection is broken and the second driving member moves across said gap toward the first driving member with the end portion of the second driving member contacting the base portion of the first driving member as the end portion of the first driving member is contacted by the base portion of the second driving member for urging the first driving member towards the chamber orifice to expel fluid therefrom.

12. The nozzle assembly of claim 11, wherein the plunger is substantially cylindrical, and each of the end portions is configured and dimensioned to occupy less than half the cross-sectional area of the plunger, wherein the first and second end portions are positioned in subjacent relation after the second member moves across the gap.

13. The nozzle assembly according to claim 11, wherein the frangible connection has a smaller cross-sectional area than either of the first and second driving members.

14. The nozzle assembly according to claim 11, wherein the first driving member has a seal in contact with an inner wall of the chamber to prevent fluid from exiting the chamber around the first driving member and through the open end.

15. The nozzle assembly according to claim 11, wherein the chamber includes a connector adapted for connecting the nozzle to the injector.

16. The nozzle assembly according to claim 11, wherein the frangible connection is disposed perpendicular to the longitudinal axis of the end portions of the first and second driving members.

17. The nozzle assembly according to claim 11 wherein the second driving member includes an end post which can be grasped to move the second driving member in a direction away from the chamber orifice to either draw fluid into the chamber or to remove the second driving member from the chamber.

18. A nozzle assembly adapted for use with an injector device comprising:

a chamber for holding a fluid and having first and second ends with an orifice at the first end for passage of the fluid and being open at the second end; and a plunger slidingly received in said chamber for expelling fluid out of or drawing fluid into the chamber by moving the plunger relative to the chamber, the plunger comprising first and second driving members and a frangible connection therebetween, with the second driving member being spaced apart from the first driving member by a gap, such that when a force sufficient to break the frangible connection is applied to the plunger, the frangible connection is broken and the second driving member moves across said gap toward the first driving member for urging the first driving member towards the chamber orifice to expel fluid therefrom, wherein the first and second driving members are cylindrical and have substantially D-shaped end portions which face each other and are joined by the frangible connection.

19. The nozzle assembly according to claim 18 wherein the frangible connection is a rectangular bridge connecting straight sides of the D-shaped portions of the first and second driving members.

20. The nozzle assembly according to claim 11 wherein the nozzle is color coded with a specific color corresponding to a predetermined width of said gap.

* * * * *